United States Patent [19]

Petitpierre et al.

[11] 4,254,032
[45] Mar. 3, 1981

[54] CARBAZOLYLMETHANE COMPOUNDS

[75] Inventors: Jean C. Petitpierre, Kaiseraugst; Peter Burri, Reinach, both of Switzerland

[73] Assignee: Ciba-Geigy Corporation, Ardsley, N.Y.

[21] Appl. No.: 29,593

[22] Filed: Apr. 12, 1979

[30] Foreign Application Priority Data

Apr. 24, 1978 [CH] Switzerland ............... 4389781/78

[51] Int. Cl.³ .................................... C07D 209/80
[52] U.S. Cl. .................................. 260/315; 282/27.5
[58] Field of Search ................................. 260/315

[56] References Cited

U.S. PATENT DOCUMENTS

| | | | |
|---|---|---|---|
| 3,527,517 | 9/1970 | Hachmans | 96/98 |
| 3,957,288 | 5/1976 | Lemahien et al. | 282/27.5 |
| 3,958,815 | 5/1976 | Poof et al. | 282/27.5 |
| 3,995,088 | 11/1976 | Garner et al. | 428/323 |
| 4,054,718 | 10/1977 | Garner et al. | 428/454 |
| 4,154,463 | 5/1979 | Burri | 260/315 |

Primary Examiner—Henry R. Jiles
Assistant Examiner—R. W. Ramsuer
Attorney, Agent, or Firm—Edward McC. Roberts; Prabodh I. Almaula

[57] ABSTRACT

Carbazolylmethane compounds of the formula

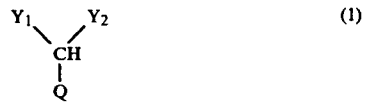

(1)

wherein one of $Y_1$, $Y_2$ and Q represents a 3-carbazolyl radical of the formula

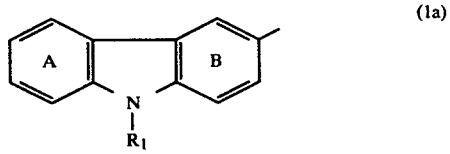

(1a)

and each of the other two independently represents an amino-substituted phenyl radical of the formula

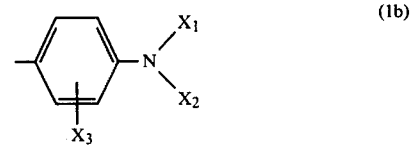

(1b)

a 3-indolyl radical of the formula

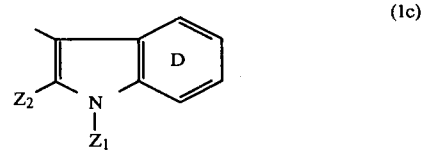

(1c)

a 3-carbazolyl radical of the formula

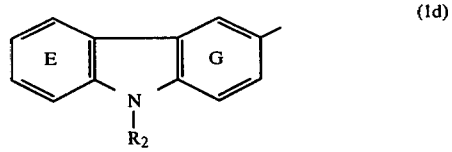

(1d)

or a 3-carbazolyl radical of the formula (1a), and Q also represents hydrogen, alkyl of 1 to 12 carbon atoms, alkenyl containing not more than 12 carbon atoms, aryl, aralkyl or a further heterocyclic radical, while each of $X_1$ and $X_2$ independently represents hydrogen, alkyl containing not more than 12 carbon atoms which is unsubstituted or substituted by halogen, hydroxyl, cyano or lower alkoxy, or represents cycloalkyl, phenyl, benzyl, or phenyl or benzyl which is substituted by halogen, lower alkyl or lower alkoxy, or $X_1$ and $X_2$ together with the nitrogen atom to which they are attached represent a 5- or 6-membered heterocyclic radical, $X_3$ represents hydrogen, halogen, nitro, lower alkyl, or lower alkoxy, each of $R_1$, $R_2$ and $Z_1$ independently represents hydrogen, alkyl containing not more than 12 carbon atoms which is unsubstituted or substituted by halogen, hydroxyl, cyano or lower alkoxy, or represents alkenyl containing not more than 12 carbon atoms, acyl of 1 to 12 carbon atoms, phenyl, benzyl, or phenyl or benzyl which is substituted by halogen, lower alkyl, lower alkoxy or nitro, and $Z_2$ represents hydrogen, lower alkyl or phenyl, the ring A is substituted by phenyl or at least one fused benzene nucleus, and the phenyl radical, the fused benzene nucleus and the rings B, D, E and G, each independently of the other, are unsubstituted or substituted by cyano, nitro, halogen, lower alkyl, lower alkoxy or lower alkoxycarbonyl; these compounds are particularly suitable for use as color formers in pressure-sensitive or heat-sensitive recording material.

5 Claims, No Drawings

CARBAZOLYLMETHANE COMPOUNDS

The present invention relates to novel carbazolylmethane compounds, a process for their manufacture and their use as colour formers in pressure-sensitive or heat-sensitive recording material.

The carbazolylmethane compounds of the invention have the general formula

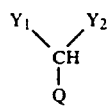                                        (1)

wherein one of $Y_1$, $Y_2$ and Q represents a 3-carbazolyl radical of the formula

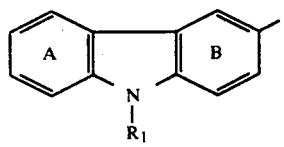                                        (1a)

and each of the other two independently represents an amino-substituted phenyl radical of the formula

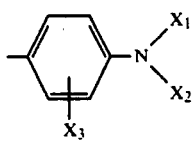                                        (1b)

a 3-indolyl radical of the formula

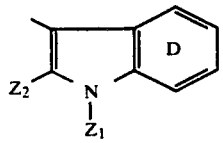                                        (1c)

a 3-carbazolyl radical of the formula

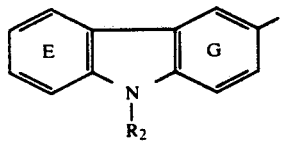                                        (1d)

or a 3-carbazolyl radical of the formula (1a), and Q also represents hydrogen, alkyl of 1 to 12 carbon atoms, alkenyl containing not more than 12 carbon atoms, aryl, aralkyl or a further heterocyclic radical, whilst each of $X_1$ and $X_2$ independently represents hydrogen, alkyl containing not more than 12 carbon atoms which is unsubstituted or substituted by halogen, hydroxyl, cyano or lower alkoxy, or represents cycloalkyl, phenyl, benzyl, or phenyl or benzyl which is substituted by halogen, lower alkyl or lower alkoxy, or $X_1$ and $X_2$ together with the nitrogen atom to which they are attached represent a 5- or 6-membered heterocyclic radical, $X_3$ represents hydrogen, halogen, nitro, lower alkyl, or lower alkoxy, each of $R_1$, $R_2$ and $Z_1$ independently represents hydrogen, alkyl containing not more than 12 carbon aoms which is unsubstituted or substituted by halogen, hydroxyl, cyano or lower alkoxy, or represents alkenyl containing not more than 12 carbon atoms, acyl of 1 to 12 carbon atoms, phenyl, benzyl, or phenyl or benzyl which is substituted by halogen, lower alkyl, lower alkoxy or nitro, and $Z_2$ represents hydrogen, lower alkyl or phenyl, the ring A is substituted by phenyl or at least one fused benzene nucleus, and the phenyl radical, the fused benzene nucleus and the rings B, D, E and G, each independently of the other, are unsubstituted or substituted by cyano, nitro, halogen, lower alkyl, lower alkoxy or lower alkoxycarbonyl.

Preferably, the ring A is substituted by one or two fused, unsubstituted or substituted benzene rings.

In the definition of the radicals of the methane compounds, lower alkyl and lower alkoxy usually denote those groups or group components which contain 1 to 5, in particular 1 to 3, carbon atoms. Lower alkyl is for example methyl, ethyl, n-propyl, isopropyl, n-butyl, sec-butyl, tert-butyl, or amyl, and lower alkoxy is for example methoxy, ethoxy or isopropoxy.

The term "aryl" denotes preferably phenyl. The acyl radical is in particular formyl, lower alkylcarbonyl, for example acetyl or propionyl, or benzoyl. Further acyl radicals are lower alkylsulfonyl, for example methylsulfonyl or ethylsulfonyl, and phenylsulfonyl. Phenyl, benzoyl and phenylsulfonyl can be substituted for example by halogen, methyl, methoxy or ethoxy.

Halogen in connection with the substituents of formula (1) is, for example, fluorine, bromine or, preferably, chlorine.

The radicals $Y_1$ and $Y_2$ can be different; but preferably they are identical. Q is preferably a 3-carbazolyl radical of the formula (1a).

Alkyl radicals represented by $R_1$, $R_2$, $X_1$, $X_2$ and $Z_1$ can be straight-chain or branched. Examples of such alkyl radicals are: methyl, ethyl, n-propyl, isopropyl, n-butyl, sec-butyl, n-hexyl, n-octyl or n-dodecyl.

Substituted alkyl radicals represented by $R_1$, $R_2$, $X_1$, $X_2$ and $Z_1$ are in particular cyanoalkyl, haloalkyl, hydroxyalkyl, alkoxyalkyl, each containing a total of 2 to 4 carbon atoms, for example $\beta$-cyanoethyl, $\beta$-chloroethyl, $\beta$-hydroxyethyl, $\beta$-methoxyethyl or $\beta$-ethoxyethyl.

Cycloalkyl represented by $X_1$ and $X_2$ is for example cyclopentyl or preferably cyclohexyl.

Preferred substituents in the benzyl and phenyl moiety of the radicals X, $Z_1$ and R are for example halogen atoms, methyl or methoxy groups. Examples of such araliphatic and aromatic radicals are: p-methylbenzyl, o- or p-chlorobenzyl, o- or p-tolyl, xylyl, o-, m- or p-chlorophenyl or o- or p-methoxyphenyl.

A heterocyclic radical represented by $X_1$ and $X_2$ together with the nitrogen atom to which they are attached is for example pyrrolidino, piperidino, pipecolino, morpholino, thiomorpholino or piperazino.

Alkenyl represented by $R_1$ and $Z_1$ is for example allyl, 2-methallyl, 2-ethallyl, 2-butenyl or octenyl.

An acyl radical within the definition of $R_1$, $R_2$ and $Z_1$ is for example formyl, or in particular lower alkylcarbonyl, for example acetyl or propionyl, or also benzoyl. Benzoyl can be substituted in the benzene ring by halogen, methyl or methoxy.

Each of $X_1$, $X_2$ and $Z_1$ independently represents preferably lower alkyl or benzyl, whilst $Z_2$ preferably represents methyl or phenyl. Advantageously, $X_1$ and $X_2$ can also represent phenyl or lower alkoxyphenyl. $X_3$ preferably represents hydrogen, methyl, methoxy or chlorine. $R_1$ and $R_2$ are preferably alkyl of 1 to 8 carbon atoms or benzyl and, in particular, ethyl, n-butyl or n-octyl.

As an alkyl or alkenyl radical, Q can have the same meanings as have been given for the radicals R, each of which is preferably substituted by an aryl radical, for example phenyl, to form an aralkyl or aralkenyl radical containing preferably 1 to 4 carbon atoms in the aliphatic portion, for example in the benzyl, piperonyl or styryl groups.

An aryl radical represented by Q can be phenyl, diphenyl or naphthyl. These aromatic carbocyclic groups, and especially phenyl, can contain halogen, cyano, nitro, lower alkyl, lower alkoxy, methylenedioxy or acyl of 1 to 8 carbon atoms. Particularly preferred acyl radicals are alkanoyl radicals of 2 to 4 carbon atoms, such as acetyl or propionyl.

As an aryl radical, Q is preferably phenyl or phenyl which is substituted by halogen, methoxy or methyl. Examples of these aryl radicals are: phenyl, o-, m- or p-methylphenyl, o-, m- or p-methoxyphenyl, o-, m- or p-chlorophenyl, o-, m- or p-bromophenyl or o-, m- or p-fluorophenyl, 3,4-dimethoxyphenyl, 3,4-dichlorophenyl, and naphthyl.

As a further heterocyclic radical, Q represents advantageously a 5- or 6-membered heterocyclic ring of aromatic character which preferably contains oxygen, sulfur or nitrogen. Examples of such heterocyclic rings are: thienyl, furyl, pyrrolyl, pyrazolyl, pyrazolonyl, triazolyl, pyridyl, thiazinyl or oxazinyl. In this connection, Z can also represent a radical which is derived from polynuclear condensed heterocyclic rings which preferably contain a condensed benzene or naphthalene ring, and is for example an unsubstituted or substituted benzothiophene, indazole, benzothiazole, benzotriazole, naphthotriazole, quinoline, phenothiazine, or phenoxazine radical. These mononuclear or polynuclear heterocyclic radicals can contain the above mentioned substituents, in particular halogen atoms, hydroxyl, cyano, amino, nitro, alkyl of 1 to 8 carbon atoms, lower alkoxy, lower alkylcarbonyl, phenyl or benzyl. Preferred heterocyclic radicals represented by Q are 3-carbazolyl, N-benzyl-3-carbazolyl or N-lower alkyl-3-carbazolyl, for example N-methyl-3-carbazolyl, N-n-butyl-3-carbazolyl or, in particular, N-ethyl-3-carbazolyl. Further preferred examples, of heterocyclic radicals Q are: 2-furyl, 2-thienyl, 4-pyridyl, 2-N-methylpyrrolyl, 3-indolyl, 2-lower alkyl-3-indolyl, 2-phenyl-3-indolyl, 1-acetyl-3-indolyl, 1-lower alkyl-2-methyl-indolyl, such as 1-ethyl-2-methyl-indolyl, 1-phenyl-3-methyl-5-pyrazolon-4-yl, 1-phenyl-3-methyl-5-amino-pyrazol-4-yl and 1-methyl-2,4-dioxoquinolinyl.

The ring A can contain one or two fused benzene nuclei which thus complete a 1,2-benzocarbazole, 2,3-benzocarbazole, 3,4-benzocarbazole (naphthophenocarbazole), 1,2;3,4-dibenzocarbazole (9,10-phenanthrocarbazole ring), 2,3;3,4-dibenzocarbazole or 1,2;2,3-dibenzocarbazole ring. Preferably, the ring A completes a 3,4-benzocarbazole radical.

The fused benzene rings of A, and the rings B, D. E and G are preferably not further substituted or, if they do contain substituents, each independently is substituted in particular by halogen, lower alkyl or lower alkoxy, for example by chlorine, methyl or methoxy. Advantageously, each benzene ring can contain 1 or 2 substituents. The substituents of the rings D and E are preferably in the para-position to the nitrogen atom.

Carbazolylmethane compounds having an important utility have the general formulae

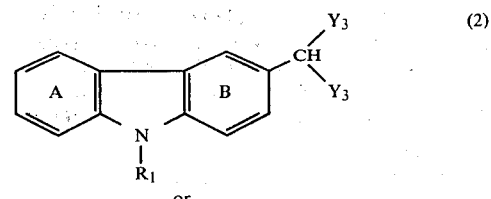 (2)

or

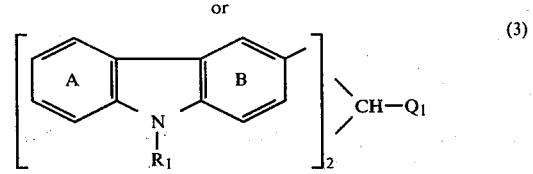 (3)

wherein A, B and $R_1$ are as defined above, $Y_3$ represents a radical of the formulae (1a), (1b), (1c) and (1d), $Q_1$ represents hydrogen, alkyl of 1 to 12 carbon atoms, alkenyl containing not more than 12 carbon atoms, aryl, aralkyl, a radical of the formulae (1a), (1b), (1c), (1d) or a further heterocyclic radical.

Preferred carbazolylmethane compounds of the formula (2) are those in which the radicals $Y_3$ are amino-substituted phenyl radicals of the formula (1b) or 3-carbazolyl radicals of the formula (1a). In the formula (3), $Q_1$ represents preferably aryl, an amino-substituted phenyl radical of the formula (1b) or a 3-indolyl radical of the formula (1c).

Particularly interesting carbazolylmethane compounds are those of the formulae

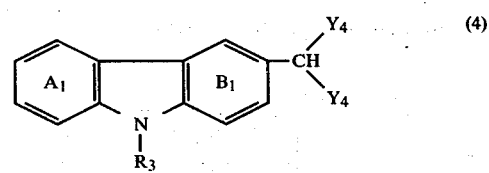 (4)

or

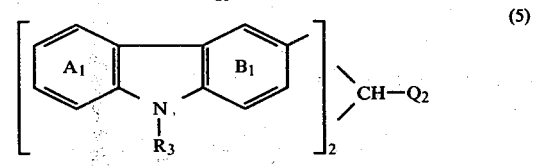 (5)

wherein $Y_4$ represents an amino-substituted phenyl radical of the formula

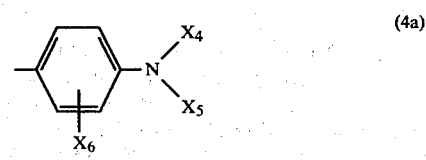 (4a)

a 3-indolyl radical of the formula

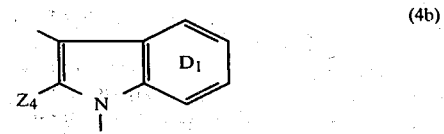 (4b)

or a 3-carbazolyl radical of the formula

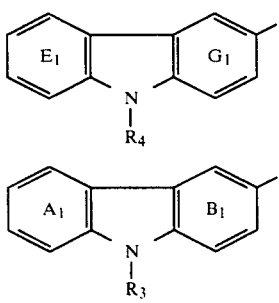
(4c), (4d)

in which formulae each of $X_4$ and $X_5$ independently represents lower alkyl, phenyl, lower alkoxyphenyl or benzyl and $X_4$ also represents hydrogen, or $X_4$ and $X_5$ together with the nitrogen atom to which they are attached represent pyrrolidino, piperidino or morpholino, $X_6$ represents hydrogen, halogen, lower alkyl or lower alkoxy, each of $R_3$, $R_4$ and $Z_3$ independently represents hydrogen, alkyl of not more than 12 carbon atoms which is unsubstituted or substituted by halogen, cyano or lower alkoxy; lower alkylcarbonyl, phenyl or benzyl which is unsubstituted or substituted by halogen, lower alkyl or lower alkoxy, $Z_4$ represents hydrogen, methyl or phenyl and $Q_2$ represents aryl, a radical of the formulae (4a), (4b) or (4c) or a further heterocyclic radical, and the ring $A_1$ contains one or two fused benzene rings and the rings $B_1$, $D_1$, $E_1$ and $G_1$, each independently of the other, are unsubstituted or substituted by cyano, halogen, lower alkyl or lower alkoxy. $Q_2$ as aryl represents in particular an aryl radical selected from phenyl, diphenyl and naphthyl which may be substituted by halogen, nitro, lower alkyl or lower alkoxy and, as further heterocyclic radical, $Q_2$ preferably represents furyl, thienyl, pyrrolyl, pyrazolyl, aminopyrazolyl, pyrazolonyl, pyridyl or quinolyl, which can be substituted by halogen, hydroxyl, cyano, nitro, alkyl of 1 to 8 carbon atoms, lower alkoxy, benzyl or phenyl.

Preferably, $Q_2$ represents a radical of the formula (4a). Particularly valuable carbazolylmethane compounds of the above formulae (1) to (5) are those mono-, bis- and tris-carbazolylmethane compounds listed hereinafter under A, B, C, D and E:

A. Mono-carbazolylmethane compounds of the formula

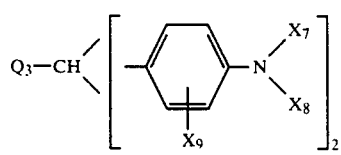
(6)

wherein $Q_3$ represents a benzocarbazol-3-yl radical of the formula

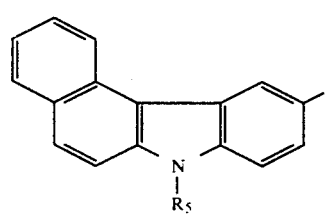
(11a)

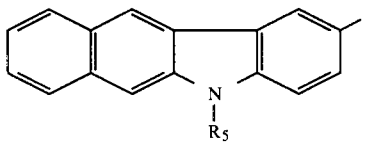
(11b)

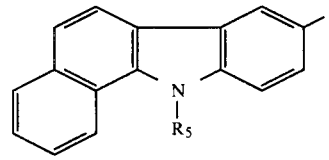
(11c)

or

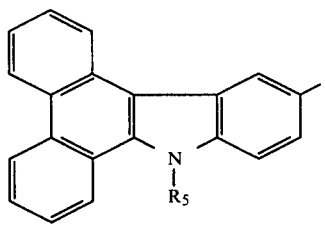
(11d)

wherein $R_5$ represents alkyl of 1 to 8 carbon atoms, acetyl or benzyl, $X_7$ represents lower alkyl, phenyl, lower alkoxyphenyl or benzyl, $X_8$ represents hydrogen, lower alkyl or benzyl, and $X_9$ represents hydrogen, methyl or methoxy.

B. Mono-carbazolylmethane compounds of the formula

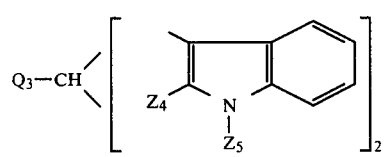
(7)

wherein $Q_3$ is as defined in formula (6), $Z_4$ represents hydrogen, methyl or phenyl and $Z_5$ represents hydrogen, alkyl of 1 to 8 carbon atoms, acetyl, benzyl or phenyl.

C. Bis-carbazolylmethane compounds of the formula

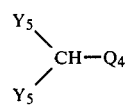
(8)

wherein $Q_4$ represents phenyl or phenyl which is substituted by halogen, lower alkyl, lower alkoxy or the amino group

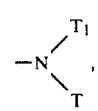

wherein $T_1$ represents lower alkyl, phenyl or lower alkoxyphenyl and $T_2$ represents hydrogen or lower alkyl, and each of $Y_5$ represents a benzocarbazol-3-yl radical of the formula (11a), (11b), (11c) or (11d).

D. Bis- or tris-carbazolylmethane compounds of the formula

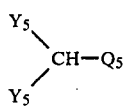 (9)

wherein Q$_5$ represents furyl, thienyl, pyrazolonyl which can be substituted by lower alkyl and/or phenyl; pyridyl; pyrrolyl, indolyl or carbazolyl, each of which can be substituted, preferably at the nitrogen atom, by lower alkyl, lower alkylcarbonyl, phenyl or benzyl.

E. Tris-carbazolylmethane compounds of the formula

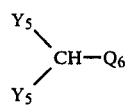 (10)

wherein each of Y$_5$ and Q$_6$ has the same meanings as Q$_3$ in formula (6).

Preferred carbazolylmethane compounds are those of the formulae (6), (8) or (10), wherein each of Q$_3$, Q$_6$ and Y$_5$ independently represents a radical of the formula (11a).

The carbazolylmethanes of the formula (1) can be obtained by reacting 1 mole of an aldehyde of the formula

Q—CHO (12)

with 1 mole of each of the compounds of the formulae

Y$_1$—H (13a) and Y$_2$—H (13b)

wherein Q, Y$_1$ and Y$_2$ have the given meanings.

A preferred process for the manufacture of symmetrical compounds of the formula (1), wherein Y$_1$ and Y$_2$ are identical, consists in reacting 1 mole of the aldehyde of the formula (12) with 2 moles of a compound of the formula (13a) or (13b).

The reaction is advantageously carried out at a temperature of 20° to 130° C., preferably 70° to 115° C. and in the presence of sulfuric acid, preferably 70 to 98% sulfuric acid. The reaction time depends on the temperature and is usually from 1 to 8 hours. To promote the solubility of the reagents and the product, it is possible to add lower aliphatic carboxylic acids or alcohols, for example acetic acid or isopropyl alcohol, to the reaction mixture, in which case the reaction temperature is from 20° C. to the reflux temperature of the mixture. In some cases it is advantageous to add urea in order to shorten the reaction time and to increase the yield. Instead of sulfuric acid, it is possible to use for example hydrochloric acid, zinc chloride, iron (III) chloride, aluminium chloride, polyphosphoric acid, phosphorus oxychloride, thionyl chloride or phosphorus pentoxide. It is often advantageous to use acetic anhydride both as reagent and as solvent. In this case, if for example Q, Y$_1$ or Y$_2$ represents an unsubstituted indolyl or carbazolyl radical at the nitrogen atom, an acetyl group can be introduced at the nitrogen atom during the reaction. The reaction can also be carried out in a water-insoluble solvent, using for example phosphorus oxychlorid or catalytic amounts of an organic sulfonic acid, for example p-toluenesulfonic acid.

The isolation of the end product of the formula (1) can be effected in a manner which is known per se, for example by pouring the reaction mixture into ice-water, if appropriate while neutralising the acid with an alkaline compound, for example ammonia, an alkali metal hydroxide or an alkali metal carbonate, collecting the precipitate by filtration or evaporating off the water-insoluble solvent, and by washing and drying the product, as well as, if appropriate, by chromatography or recrystallisation of the product, which in certain cases can contain insignificant amounts of polycondensation products.

Carbazolylmethanes of the formula (1) can be obtained, for example, by reacting 1 mole of an aldehyde of the formula

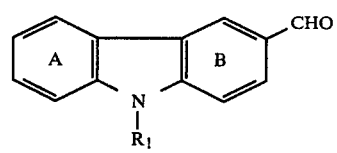 (14)

with 2 moles of a compound of the formulae

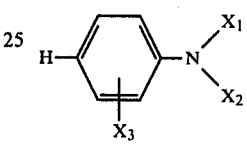 (15),

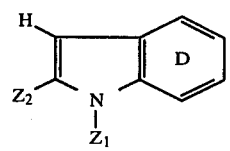 (16),

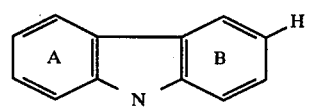 (17), or

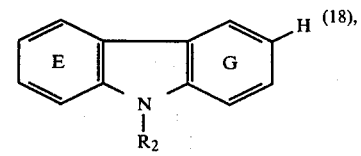 (18), or reacting 1 mole of an aldehyde of the formula

Q$_1$—CHO, (19)

with 2 moles of a carbazolyl compound of the formula (17), wherein A, B, D, E, G, R$_1$, R$_2$, X$_1$, X$_2$, X$_3$, Z$_1$, Z$_2$ and Q$_1$ have the given meanings.

The aldehydes of the formulae (12), (14) and (19) can be obtained in accordance with German Auslegeschrift 1,060,375, U.S. Pat. No. 2,558,285 or J. Org. Chem., Vol. 30, 3714–3718, (1965), by formylation of the compounds Q—H with dialkylformamides in the presence of an acid halide, and they can be used direct without being isolated.

The carbazolylmethane compounds of the formula (1) to (10) are normally colourless or faintly coloured. When these colour formers are brought into contact with an acid developer, i.e. an electron acceptor, then, depending on the meaning of Y$_1$ and Y$_2$, they produce intense orange, red, violet, blue and green shades of excellent lightfastness. They are therefore also very useful when mixed with one or more other known colour formers, for example 3,3-(bis-aminophenyl)-phthalides, 3,3-(bis-indolyl)-phthalides, 3-aminofluoranes, 2,6-diaminofluoranes or spiropyranes, to produce blue, navy blue, grey or black colourations.

The carbazolylmethane compounds of the formula (1) to (10) exhibit both on clay and on phenolic substrates an improved colour intensity and lightfastness. They are suitable in particular as slowly developing colour formers for use in a pressure-sensitive recording material, which can also be a copying material.

A pressure-sensitive material consists for example of at least one pair of sheets, which contain at least one colour former of the formulae (1) to (10) dissolved in an organic solvent, and a solid electron acceptor as developer. The colour former effects a coloured marking at those points when it comes into contact with the electron acceptor.

Typical examples of such developers are bentonite, silton clay (acid modified bentonite), attapulgite clay, halloysite, montmorillonite, silica, alumina, aluminium sulphate, aluminium phosphate, zinc chloride, kaolin or any clay or organic compound with acid reaction, for example unsubstituted or ring-substituted phenols, salicylic acid or salicylates and their metal salts, or an acid polymeric material, for example a phenolic polymer, an alkylphenolacetylene resin, a maleic acid/colophonium resin or a partially or completely hydrolysed polymer of maleic acid and styrene, ethylene or vinyl methyl ether, or carboxypolymethylene. Mixtures of these polymeric compounds can also be used. Preferred developers are attapulgite clay, silton clay, zinc salicylate or a phenolformaldehyde resin, such as condensation products of p-substituted phenols with formaldehyde. These electron acceptors are preferably applied in the form of a layer to the face of the receiver sheet. According to the invention, these developers and, in particular, attapulgite clay and silton clay, can be applied to paper not only in the customary alkaline to neutral range, for example at pH values of 7 to 12, preferably 8 to 10, but also in the acid range, for example at pH values from 3 to 6.9, preferably 4 to 6. In the acid range, the carbazolylmethane compounds have a higher rate and colour intensity during the colour development.

In order to prevent the colour formers contained in the pressure-sensitive recording material from becoming active too soon, they are usually separated from the electron acceptor. This can advantageously be accomplished by incorporating the colour formers in foamlike, sponge-like or honeycomb-like structures. Preferably, however, the colour formers are enclosed in microcapsules, which as a rule can be ruptured by pressure.

When the capsules are ruptured by pressure, for example with a pencil, and the colour former solution is transferred in this manner to an adjacent sheet which is coated with an electron acceptor, a coloured area is produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin, for example chloroparaffin or polyhalogenated diphenyl, such as trichlorodiphenyl, and also tricresyl phosphate, di-n-butyl phthalate, dioctyl phthalate, trichlorobenzene, trichloroethyl phosphate, aromatic ethers, such as benzylphenyl ether, hydrocarbon oils, such as paraffin, alkylated derivatives of diphenyl, naphthalene or triphenyl, terphenyl, dibenzyl toluene, partially hydrogenated terphenyl, or other chlorinated or hydrogenated, condensed aromatic hydrocarbons.

The capsule walls can be formed evenly around the droplets of the colour former solution by coacervation, and the encapsulating material can consist of gelatin and gum arabic, as described e.g. in U.S. Pat. No. 2,800,457. The capsules can be formed also from an aminoplast by polycondensation, as described in British Pat. Nos. 989,264, 1,156,725, 1,301,052 and 1,355,124.

The microcapsules containing the colour formers of formula (1) can be used for the manufacture of a wide variety of known kinds of pressure-sensitive copying material. The various systems differ substantially from one another in the arrangement of the capsules, the colour reactants and the support.

A preferred arrangement is that in which the encapsulated colour former is applied as a layer to the back of a transfer sheet and the electron acceptor as a layer to the face of a receiver sheet. However, the components can also be used in the paper pulp.

Another arrangement of the constituents consists in the microcapsules which contain the colour former, and the developer, being in or on the same sheet, in the form of one or more individual sheets or being present in the paper pulp.

Such pressure-sensitive copying materials are described, for example, in U.S. Pat. Nos. 2,730,457, 2,932,582, 3,418,250, 3,427,180 and 3,516,846. Further systems are described in British Pat. Nos. 1,042,596, 1,042,597, 1,042,598, 1,042,599 and 1,053,935. Microcapsules which contain the colour formers of formula (1) are suitable for each of these systems and for other pressure-sensitive systems.

The capsules are preferably secured to the support by means of a suitable adhesive. Since paper is the preferred support, these adhesives are principally paper coating agents, for example gum arabic, polyvinyl alcohol, hydroxymethyl cellulose, casein, methyl cellulose or dextrin.

As paper, there is used not only normal paper made from cellulose fibres, but also paper in which the cellulose fibres are replaced (partially or completely) by synthetic polymer fibres.

The carbazolylmethane compounds of the formula (1) to (10) can also be used as colour formers in a thermoreactive recording material. This recording material contains normally at least one carrier, one colour former, one solid electron acceptor and, if appropriate, also a binder. Thermoreactive recording systems comprise for example heat-sensitive recording and copying materials and papers. These systems are used, for example, for recording information, e.g. in electronic computers, teleprinters or telewriters, and in measuring instruments. The image (mark) formation can also be effected manually with a heated pen. Laser beams can also be used to produce heat-induced marks. The thermoreactive recording material can be so composed that the colour former is dispersed or dissolved in one binder layer and the developer is dissolved or dispersed in the binder in a second layer. A second possibility consists in dispersing both the colour former and the developer in one layer. By means of heat the binder is softened at specific areas and the colour former comes into contact with the electron acceptor at those points where heat is applied and the desired colour develops at once.

Suitable developers are the same electron acceptors as are used in pressure-sensitive papers. Examples of developers are the clays and phenolic resins already mentioned, or phenolic compounds, for example 4-tert-butylphenol, 4-phenylphenol, 4-hydroxydiphenyl ether, α-naphthol, β-naphthol, 4-hydroxymethylbenzoate, 4-hydroxyacetophenone, 2,2'-dihydroxydiphenyl, 4,4-isopropylidenediphenol, 4,4'-isopropylidene-bis-(2-methylphenol), 4,4'-bis-(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid and organic, preferably aliphatic, dicarboxylic acids, for example tartaric acid, oxalic acid, maleic acid, citric acid, citraconic acid and succinic acid.

Fusible, film-forming binders are preferably used for the manufacture of the thermoreactive recording material. These binders are normally water-soluble, whereas the carbazolylmethane compounds and the developers are insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are hydrophilic polymers, for example polyvinyl alcohol, polyacrylic acid, hydroxyethyl cellulose, methyl cellulose, carboxymethyl cellulose, polyacrylamide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylmethacrylates, ethyl cellulose, nitrocellulose and polyvinyl carbazole. The preferred arrangement, however, is that in which the colour former and the developer are contained in one layer in a water-soluble binder.

The thermoreactive coatings can contain further ingredients. To improve the degree of whiteness, to facilitate the printing of papers, and to prevent the heated pen from sticking, the coatings can contain, for example, talc, $TiO_2$, ZnO or $CaCO_3$ or also organic pigments, for example urea/formaldehyde polymers. In order to effect the colour formation only within a limited temperature range, it is possible to add substances such as urea, thiourea, acetamide, acetanilide, stearic amide, phthalic anhydride, phthalic nitrile or other appropriate fusible products which induce the simultaneous melting of the colour former and developer. Thermographic recording materials preferably contain waxes.

In the following Examples, which further illustrate the present invention, the percentages are by weight unless otherwise indicated.

EXAMPLE 1

49.1 g of N-ethyl-3,4-benzocarbazole are dissolved in 23.2 g of dimethyl formamide and 50 ml of ethylene chloride. With stirring, 46 g of phosphorus oxychloride are added to this solution in such a manner that the temperature does not exceed 30° C. The temperature is raised to 65°–70° C. in the course of 2 hours and kept thereat for 8 hours. The reaction mixture is then allowed to cool to 50° C. and 14.4 ml of water are added, whereupon the temperature rises rapidly to 70° C. The reaction solution is subsequently stirred for 30 minutes and the introduction of nitrogen is commenced. To the solution are added 100 ml of ethylene chloride and 65.9 g of N-methyl-diphenylamine. After stirring for 16 hours at 65°–70° C. under nitrogen, the condensation is complete. After cooling, the solution is adjusted to pH 7 with 18% aqueous sodium hydroxide solution.

The organic phase is separated, washed with two 200 ml portions of water and dried over calcined sodium sulphate. With stirring, the dried ethylene chloride solution is poured into 1500 ml of methanol, whereupon the product precipitates. The precipitate is removed by filtration and dried in vacuo at 50° C., affording 68 g of the compound of the formula

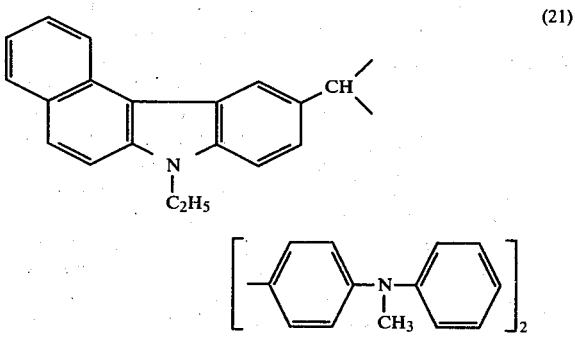

The compounds melts at 240°–247° C. (decomposition). This colour former slowly develops an intense blue colour on silton clay.

EXAMPLE 2

The compound of the formula

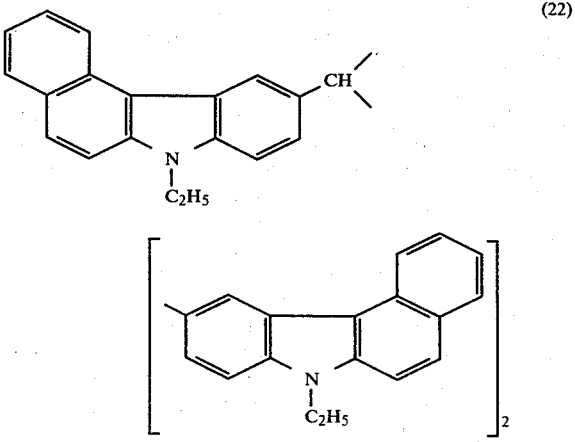

is obtained by repeating exactly the procedure of Example 1 using 88.2 g of N-ethyl-3,4-benzocarbazole instead of N-methyl-diphenylamine. The compound slowly develops an intense blue colour on silton clay.

EXAMPLE 3

The compound of the formula

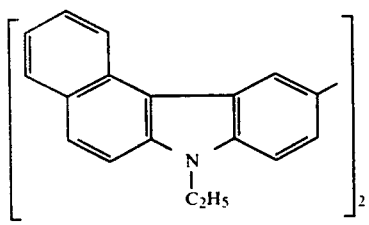

(23)

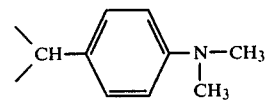

is obtained by repeating exactly the procedure of Example 1 using 31.2 g of N,N-dimethylaniline instead of N-ethyl-3,4-benzocarbazole and 88.2 g of N-ethyl-3,4-benzocarbazole instead of N-methyl-diphenylamine.

This compound melts at 212°–214° C. It slowly develops an intense blue colour on silton clay.

The following compounds are obtained in the same manner as described in Example 1:

| Formula | Shade on silton clay |
|---|---|
| (24) | blue |
| (25) | blue |
| (26) | blue |
| (27) | red |
| (28) | red |
| (29) | blue |
| (30) | blue |

| Formula | Shade on silton clay |
|---|---|
| (31) [structure: bis(N-ethyl-benzocarbazolyl) linked via CH to N-ethyl-carbazole] | blue |

EXAMPLE 4

4.2 g of N-methylanilino-benzaldehyde and 9.8 g of N-ethyl-3,4-benzocarbazole are dissolved in 40 ml of ethylene chloride. To this solution are added 3.1 g of phosphorus oxychloride and the reaction mixture is stirred for 3 hours at 40° C. in a nitrogen atmosphere. The reaction mixture is then poured into water, neutralised with 30% ammonia solution and the ethylene chloride phase is separated. On pouring the ethylene chloride solution into methanol, the product precipitates in crystalline form. The precipitate is removed by filtration and dried in vacuo at 50° C., affording the compound of the formula (23). The following compounds can be obtained in a manner analogous to that described in this Example:

| Formula | Shade on silton clay |
|---|---|
| (32) [N-benzyl-benzocarbazolyl]₂ CH—phenyl | green |
| (33) [N-ethyl-benzocarbazolyl]₂ CH—C₆H₄—Cl | green |
| (34) [N-ethyl-benzocarbazolyl]₂ CH—C₆H₄—OCH₃ | green |

EXAMPLE 5

Manufacture of a pressure-sensitive copying paper

A solution of 3 g of the carbazolylmethane compound of formula (21) in 97 g of partially hydrogenated terphenyl is emulsified in a solution of 12 g of pigskin gelatin in 88 g of water of 50° C. A solution of 12 g of gum arabic in 88 g of water of 50° C. is then added, followed by the addition of 200 ml of water of 50° C. The resultant emulsion is poured into 600 g of ice water and cooled until the temperature is 20° C., in the course of which the coacervation is effected. A sheet of paper is coated with the resultant suspension of microcapsules and dried. A second sheet of paper is coated with silton clay as follows: 25 g of silton clay are suspended in 42 g of water and, with vigorous stirring, the pH is adjusted to 10 with 30% sodium hydroxide solution. After addition of 7.5 g of a binder, for example latex, the suspension is coated on paper and dried. The first sheet and the sheet of paper coated with silton clay are laid on top of each other with the coated sides face to face. Pressure is exerted on the first sheet by writing by hand or with a typewriter and an intense blue copy of excellent lightfastness slowly develops on the sheet coated with silton clay.

If the second sheet is coated with silton clay by adjusting a suspension of 25 g of silton clay and 42 g of water with 30% sodium hydroxide solution to a pH of 5, then 7.5 g of a binder are added, and the suspension is coated on paper, dried, and the procedure is repeated as described above, the colour former of the formula (21) develops its intense lightfast blue colour markedly more rapidly.

Corresponding intense and lightfast blue and green copies are also obtained by using each of the other colour formers of the formulae (22) to (34) indicated in the Examples.

EXAMPLE 6

Manufacture of a thermoreactive paper 6 g of an aqueous dispersion which contains 1.57% of the carbazolylmethane compound of the formula (21) and 6.7% of polyvinyl alcohol are mixed with 134 g of an aqueous dispersion which contains 14% of 4,4-isopropylidene-diphenol, 8% of attapulgite clay and 6% of polyvinyl alcohol. This mixture is applied to a paper and dried. Contacting the paper with a heated ball-point pen produces an intense blue colour of excellent lightfastness.

Intense and lightfast blue or green colours can also be obtained by using each of the other colour formers of the formulae (22) to (34).

EXAMPLE 7

In a ball mill, 32 g of bis-(4-hydroxyphenyl)-dimethylmethane (Bis-phenol A), 3.8 g of the distearylamide of ethylene diamine, 39 g of kaolin, 20 g of an 88% hydrolysed polyvinyl alcohol and 500 ml of water are ground to a particle size of about 5μ. In a second ball mill, 6 g of the compound of the formula (21), 3 g of a 88% hydrolysed polyvinyl alcohol and 60 ml of water are ground to a particle size of about 3μ.

Both dispersions are mixed and applied to paper to a dry coating weight of 5.5 g/m². An intense blue colour of excellent lightfastness is produced by contacting the paper with a heated ball-point pen.

What is claimed is:
1. A carbazolylmethane compound of the formula

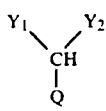  (1)

wherein Q represents a 3-carbazolyl radical of the formula

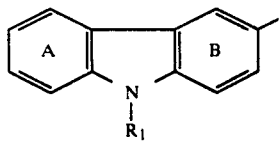  (1a)

and each of $Y_1$ and $Y_2$, independently, represents an aminosubstituted phenyl radical of the formula

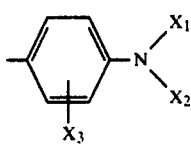  (1b)

wherein each of $X_1$ and $X_2$ independently represents hydrogen, alkyl containing not more than 12 carbon atoms which is unsubstituted or substituted by halogen, hydroxyl, cyano or lower alkoxy, or represents cyclopentyl, cyclohexyl, phenyl, benzyl, or phenyl or benzyl which is substituted by halogen, lower alkyl or lower alkoxy, $X_3$ represent hydrogen, halogen, nitro, lower alkyl, or lower alkoxy, $R_1$ represents hydrogen, alkyl containing not more than 12 carbon atoms which is unsubstituted or substituted by halogen, hydroxyl, cyano or lower alkoxy, or represents alkenyl containing not more than 12 carbon atoms, acyl of 1 to 12 carbon atoms, phenyl, benzyl, or phenyl or benzyl which is substituted by halogen, lower alkyl, lower alkoxy or nitro, and the ring A is substituted by one or two fused benzene nuclei, and the fused benzene nuclei and the ring B, each independently of the other, are unsubstituted or substituted by cyano, nitro, halogen, lower alkyl, lower alkoxy or lower alkoxycarbonyl.

2. A methane compound according to claim 1 of the formula

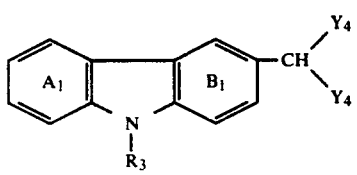  (4)

wherein $Y_4$ represents an amino-substituted phenyl radical of the formula

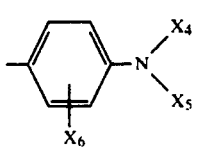  (4a)

wherein each of $X_4$ and $X_5$ independently represents lower alkyl, phenyl, lower alkoxyphenyl or benzyl and $X_4$ also represents hydrogen, $X_6$ represents hydrogen, halogen, lower alkyl or lower alkoxy, $R_3$ represents hydrogen, alkyl of not more than 12 carbon atoms which is unsubstituted or substituted by halogen, cyano or lower alkoxy; lower alkylcarbonyl, phenyl or benzyl which is unsubstituted or substituted by halogen, lower alkyl or lower alkoxy, and the ring $A_1$ contains one or two fused benzene rings and the ring $B_1$ is unsubstituted or substituted by cyano, halogen, lower alkyl or lower alkoxy.

3. A methane compound according to claim 1, wherein the ring A together with the fused benzene ring completes a 1,2-benzocarbazolyl, 2,3-benzocarbazolyl, 3,4-benzocarbazolyl, 1,2:3,4-dibenzocarbozolyl or 1,2:2,3-dibenzocarbazolyl radical, wherein the benzo moiety is unsubstituted or substituted by halogen, lower alkyl or lower alkoxy.

4. A methane compound according to claim 1, wherein $Y_1$ and $Y_2$ are identical.

5. A methane compound according to claim 2 of the formula

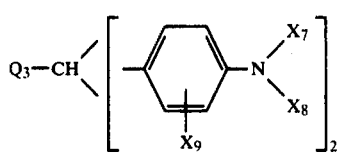  (6)

wherein $Q_3$ represents a benzocarbazol-3-yl radical of the formula

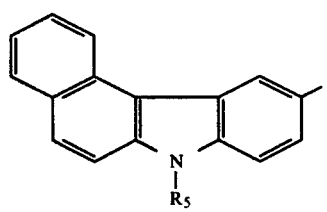  (11a)

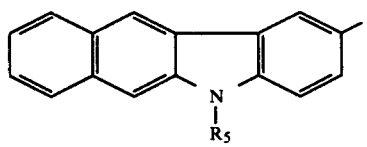  (11b)

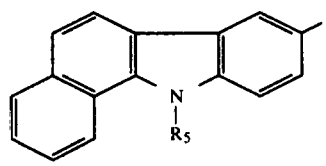  (11c)

or

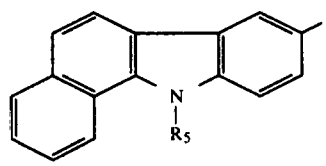  (11d)

wherein $R_5$ represents alkyl of 1 to 8 carbon atoms, acetyl or benzyl, $X_7$ represents lower alkyl, phenyl, lower alkoxyphenyl or benzyl, $X_8$ represents hydrogen, lower alkyl or benzyl, and $X_9$ represents hydrogen, methyl or methoxy.

* * * * *